(12) United States Patent
Price et al.

(10) Patent No.: US 11,712,426 B2
(45) Date of Patent: Aug. 1, 2023

(54) METALLO-LIOTHYRONINE

(71) Applicant: Synthonics, Inc., Blacksburg, VA (US)

(72) Inventors: John D. Price, Radford, VA (US); Thomas Piccariello, Blacksburg, VA (US); Michaela E. Mulhare, Christiansburg, VA (US)

(73) Assignee: SYNTHONICS, INC., Blacksburg, VA (US)

( * ) Notice: Subject to any disclaimer, the term of this patent is extended or adjusted under 35 U.S.C. 154(b) by 0 days.

(21) Appl. No.: 17/045,234

(22) PCT Filed: Apr. 4, 2019

(86) PCT No.: PCT/US2019/025725
§ 371 (c)(1),
(2) Date: Oct. 5, 2020

(87) PCT Pub. No.: WO2019/195513
PCT Pub. Date: Oct. 10, 2019

(65) Prior Publication Data
US 2021/0046032 A1    Feb. 18, 2021

Related U.S. Application Data

(60) Provisional application No. 62/652,705, filed on Apr. 4, 2018.

(51) Int. Cl.
*A61K 33/30* (2006.01)
*A61P 5/14* (2006.01)
(Continued)

(52) U.S. Cl.
CPC ............ *A61K 31/198* (2013.01); *A61K 33/00* (2013.01); *A61K 33/06* (2013.01); *A61K 33/24* (2013.01);
(Continued)

(58) Field of Classification Search
None
See application file for complete search history.

(56) References Cited

U.S. PATENT DOCUMENTS 7,989,440 B2    8/2011  Piccariello
2008/0015352 A1 1/2008  Piccariello
(Continued)

FOREIGN PATENT DOCUMENTS

AU    2013205471 B2    2/2016
JP    2002506049 A     2/2002
(Continued)

OTHER PUBLICATIONS

Greene, CD. Permanently Beat Hypothyroidism Naturally 2012; Woman's Republic:58 pages (2 pages) (Year: 2012).*
(Continued)

*Primary Examiner* — Ernst V Arnold
(74) *Attorney, Agent, or Firm* — Barnes & Thornburg LLP; Ryan L. Marshall

(57) ABSTRACT

The invention relates to supramolecular metal coordinated liothyronine (triiodothyronine, T3) compositions, methods of preparing such compositions, methods of purifying and formulating supramolecular metal coordinated liothyronine, and methods of treating hypothyroidism and other disease states using such compositions.

19 Claims, 13 Drawing Sheets

(51) Int. Cl.
  *A61K 31/198* (2006.01)
  *A61K 33/00* (2006.01)
  *A61K 33/06* (2006.01)
  *A61K 33/24* (2019.01)
  *A61K 33/34* (2006.01)
  *A61K 47/42* (2017.01)

(52) U.S. Cl.
  CPC ............ *A61K 33/30* (2013.01); *A61K 33/34* (2013.01); *A61K 47/42* (2013.01)

(56) References Cited

U.S. PATENT DOCUMENTS

| | | |
|---|---|---|
| 2012/0115823 A1 | 5/2012 | Price et al. |
| 2016/0199385 A1 | 7/2016 | Sciavolino et al. |

FOREIGN PATENT DOCUMENTS

| | | |
|---|---|---|
| JP | 2003261683 A | 9/2003 |
| JP | 2009512728 A | 3/2009 |
| JP | 2013542961 A | 11/2013 |
| JP | 2017079181 A | 4/2017 |
| WO | 2007050181 A2 | 5/2007 |
| WO | 2007099932 A1 | 9/2007 |
| WO | 2012064722 A1 | 5/2012 |
| WO | 2015167010 A1 | 11/2015 |

OTHER PUBLICATIONS

Betsy et al. (Int J Trichology 2013;5(1):40-42). (Year: 2013).*
Putattive definition [online] retrived on Aug. 1, 2022 from: https://dictionary.cambridge.org/dictionary/english/putative; 1 page. (Year: 2022).*
Conceicao et al. "Metal Coordinated Poly-Zinc-Liothyronine Provides Stable Circulating 1-22 Triiodothyronine Levels in Hypothyroid Rats" Thyroid, vol. 28 Issue 11 (Nov. 12, 2018): pp. 1425-1433.
Martinez Valeria R. et al.,Azilsartan and its Zn(II) complex. Synthesis, anticancer mechanisms of action and binding to bovin serum albumin, Toxicology in Vitro, Elsevier Science GB vol. 48, Mar. 6, 2018, pp. 205-220.
Carraher, C. E. et al., degradation of the polyamine derived from tetrachloroplatinate and methotrexate, Polymericmaterials Science and Engineering, 1987, vol. 57, pp. 173-175 (reference indicating a well-known technique).
Zhao, A. and Carraher, C. E. Jr., F MALDI MS for polymers from ciprofloxacin and organotin dihaiides, PMSE Preprints, 2007, vol. 96, pp. 390-392 (reference indicating a well-known technique).
Charraher, C. E. Jr. and Zhao, A., Modeling of moderate mass range F MALDI MS results of organotin poly(ester amines) derived from ciprofloxacin and dibutyltin dishioride, PMSE Preprints, 2011, vol. 106 (reference indicating a well-known technique).
Office Action for Japanese Application No. 2021-503706, dated Mar. 31, 2023.

* cited by examiner

Poly Metallo Amoxicillin

Poly Metallo Cefotetan

Poly Metallo Furosemide

Poly Metallo Methotrexate

Poly Metallo Tetracycline

Poly Metallo Valsartan

METALLO-LIOTHYRONINE

RELATED APPLICATIONS

This application is a National Stage application of International Application No. PCT/US2019/025725, filed Apr. 4, 2019, which claims the benefit of U.S. Provisional Patent Application No. 62/652,705, filed Apr. 4, 2018, each of which are incorporated by reference in their entirety.

BACKGROUND

Technical Field

The invention generally relates to supramolecular metal coordinated liothyronine compositions, methods of preparing such compositions, methods of purifying and formulating supramolecular metal coordinated liothyronine, and methods of treatment hypothyroidism and other disease states using such compositions.

Background Information

Medical treatment of hypothyroidism with thyroid hormone replacement therapy has a long history with little change since the introduction of Synthroid® (levothyroxine (T4)) in the 1950's. The two major hormones synthesized and secreted by the thyroid gland (triiodothyronine (T3) and T4) regulate the metabolic activity of virtually every organ in the body. Thyroid homeostasis has evolved to produce an intricately complicated, but not wholly understood, system in which hypothalamic and pituitary feedback loops participate. However, some of what has been learned in the last 60 years can be applied now to fine tune thyroid hormone replacement therapy.

Although T3 has been commercially available as a drug product (Cytomel®, liothyronine) since 1956, it is seldom used in modern regimens. Most endocrinologists and other physicians avoid T3 and prescribe only T4 since (a) endogenous enzymes convert T4 into T3 and (b) the pharmacokinetics of current T3 products may pose health risks.

Administration of T4 alone, however, does not mimic the thyroid hormone production of a healthy thyroid gland, which normally releases enough T3 to account for 15-20% of the T3 circulating in blood. Moreover, although many patients may convert enough T4 to T3 to compensate for the lack of naturally secreted T3, some patients do not. These patients often experience residual hypothyroid symptoms and report higher rates of weight gain, depression and lethargy.

Consequently, there has been much interest in studying the benefits of providing T3 along with T4 for those patients who continue to experience residual hypothyroid symptoms after taking T4 alone. Although controversy persists on when and how to utilize T3, most experts agree today that currently available T3 compounds should be administered more than once daily. In healthy individuals, T3 plasma concentrations remain relatively steady. However, when given orally as a drug product, T3 is rapidly absorbed leading initially to high peak concentrations followed by low trough levels. Multiple low doses more closely simulate natural T3 blood levels but introduce significant compliance issues. A slow release formulation is more likely to fulfill the unmet medical need for a T3 product that would provide normal 24-hour levels with once-a-day dosing.

Although pharmacy-compounded sustained release (SR) preparations are available, their bioavailability and clinical efficacy vary due to formulation limitations. An FDA-approved best-in-class SR T3 product should ultimately be accepted by the medical community as an effective therapy for a substantial portion of hypothyroid patients. In addition, T3 is being used increasingly to manage other conditions.

While acknowledging the widely known caveat that the use of thyroid hormones in euthyroid patients may result in subclinical as well as symptomatic hyperthyroidism, it is likely that the medicinal role for T3 will expand in the future. Annual sales for thyroid hormones are estimated to be over $1B. With an estimated 20% of the T4 product users being treated sub-optimally, a T3 product is likely to have significant impact.

A "euthyroid-mimetic" dosage form of liothyronine for use in thyroid hormone replacement and other therapies would be an improvement over existing regimens.

BRIEF SUMMARY

The complexes and methods described herein addresses the clinical deficiency of the currently available oral treatments for hypothyroidism. Approximately 15% of persons suffering from hypothyroidism report insufficient symptomatic improvement from levothyroxine (T4, Synthroid®) alone. This is thought to be related to a genetic variation in the enzyme that converts T4 to T3, the active form of thyroid hormone. Liothyronine (T3, Cytomel®) is believed to be too rapidly absorbed and too short-lived to act as an effective complement to T4. If the value of combining T3 with T4 is to be realized for these patients, a controlled release product producing T3 plasma concentrations like normal (euthroid) will be needed. Euthroid plasma levels are important for achieving normal thyroid hormone concentrations in all tissues. The broad, long-term objective of this product is to provide patients a new thyroid hormone drug product that can produce euthroid-like T3 levels with once daily oral dosing. The metallo-T3 complexes are designed to extend the transit time through the gastrointestinal tract where T3 molecules gradually break free from the metal complex and enter the blood stream. This modulates the rate of delivery and thereby the rate of absorption One embodiment described herein is a supramolecular metal coordination complex according to formula I:

wherein:
M is a metal atom;
D is a biologically active moiety that comprises at least two functional groups that are capable of coordinating to a divalent metal;
A is a second biologically active moiety or adjuvant;
W is $H_2O$;
x is an integer from 1 to 10;
o is an integer from 1 to 10;
p:x ratio 1/1000 to 1000/1.
q is zero or an integer from 1 to 20; and
n is an integer greater than or equal to 2.

In another embodiment, the complex of formula I is insoluble in water. In another embodiment, the complex of formula I is in the form of a polymeric structure. In another embodiment, the biologically active moiety (D) demonstrates a controlled release from the complex when administered to a patient. In one aspect, the functional groups of the biologically active moiety (D) comprises a heteroatom that forms a metal coordination bond. In another aspect, the heteroatom of that forms a metal coordination bond is selected from nitrogen, oxygen, and sulfur.

In another embodiment, the metal atom (M) of formula I is selected from s-block elements, transition metals, p-block metals, lanthanides, and actinides. In one aspect, the metal atom is selected from zinc, copper, magnesium, calcium, strontium, sodium, nickel, and bismuth.

In another embodiment, the biologically active moiety (D) includes a first functional group and a second functional group. In another embodiment, the biologically active moiety (D) includes comprises a first functional group, a second functional group, and a third functional group.

In another embodiment, the adjuvant (A) is selected from aromatic dicarboxylic acids, phenols, and catechols. In one aspect, the adjuvant is tyrosine.

In another embodiment, x and o of formula I are the same value. In another embodiment, x and o of formula I are different values.

In another embodiment, the biologically active moiety (D) is selected from triiodothyronine (T3), amoxicillin, cefotetan, furosemide, methotrexate, valsartan, chlortetracycline, demeclocycline, doxycycline, meclocycline, oxytetracycline, tetracycline, ciprofloxacin, danofloxacin, difloxacin, enoxacin, enrofloxacin, fleroxacin, lomefloxacin, marbofloxacin, norfloxacine, perfloxacin, pipemidic acid, ofloxacin, and sarafloxacin and combinations thereof. In one aspect, the biologically active moiety (D) is triiodothyronine (T3). In another aspect, the complex according to formula I is $[Zn(T3)(H_2O)]_n$, $[Zn_6(T3)(tyr)_5]_n$, $[Cu(T3)(H_2O)]_n$, $[Mg(T3)-2H_2O]_n$, $[Ca(T3)-2H_2O]_n$, and $[Sr(T3)-4H_2O]_n$.

Another embodiment is a pharmaceutical composition including the complex of formula I and a pharmaceutically acceptable carrier. In one aspect, the composition demonstrates a controlled release of the biologically active moiety.

Another embodiment is a method of treating a patient having a disease including administering a therapeutically effective amount of a complex according to formula I to the patient in need thereof. In one aspect, the disease is hypothyroidism.

Another embodiment, is a method of increasing a mucoadhesive property of a biologically active moiety including forming a metal coordination complex according to formula I.

DETAILED DESCRIPTION

Figure 1:
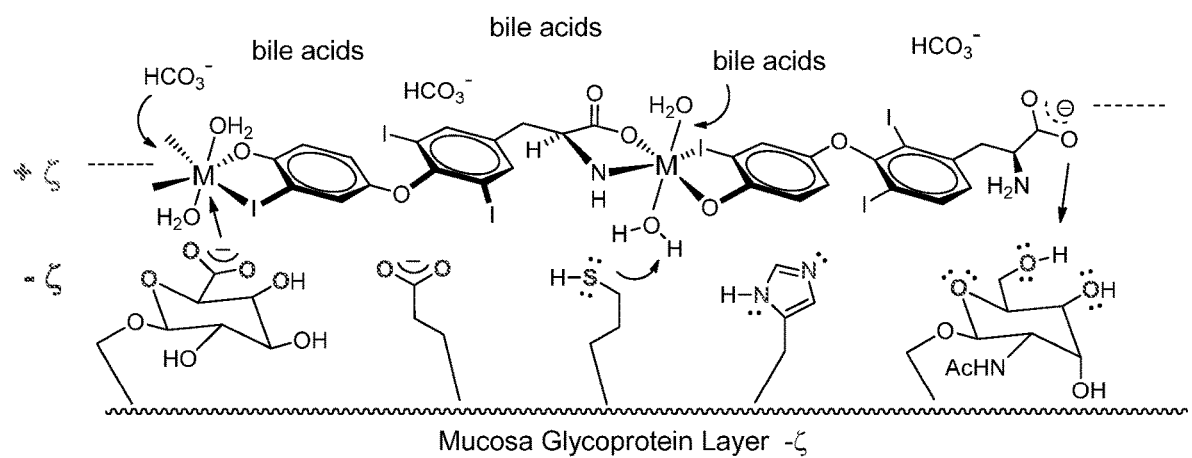
FIG. 1 is an illustration of how endogenous ligands in the upper GI tract can affect hydrolysis rate. These include HCl (stomach), bile acids and carbonate buffers (upper intestines).
Figure 2:
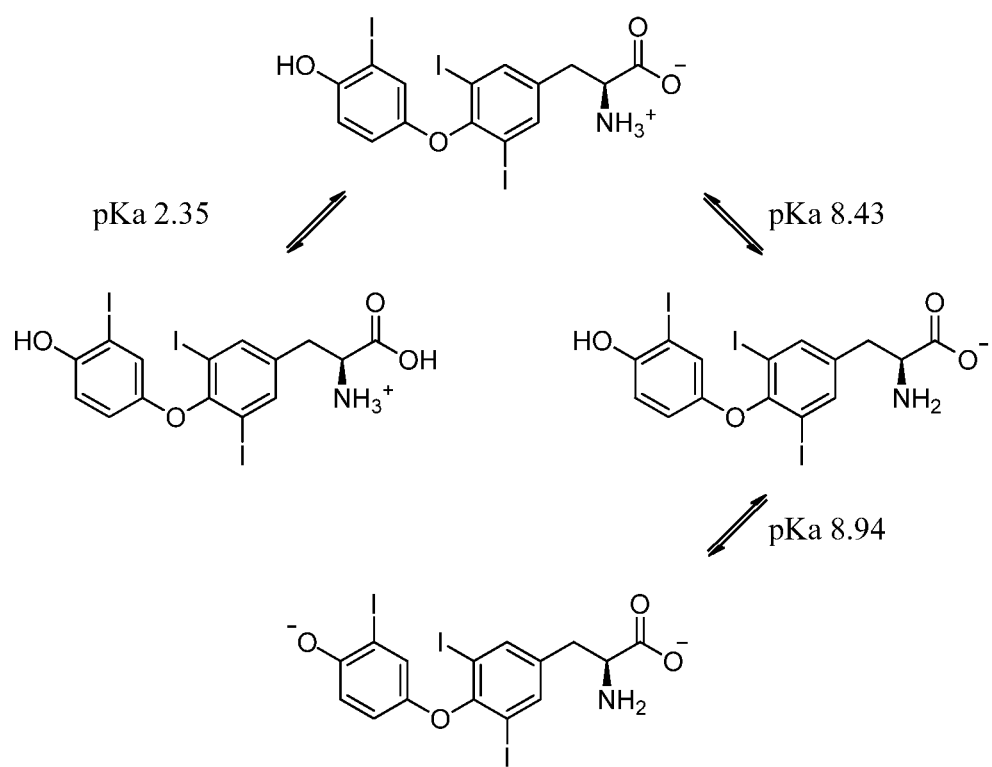
FIG. 2 is an illustration showing triiodothyronine ionizable functional groups with experimentally determined pKa values (Sirius). Species are written as $H_3T3^+$; $H_2T3$; $HT3^-$; $T3^{-2}$.
Figure 3:
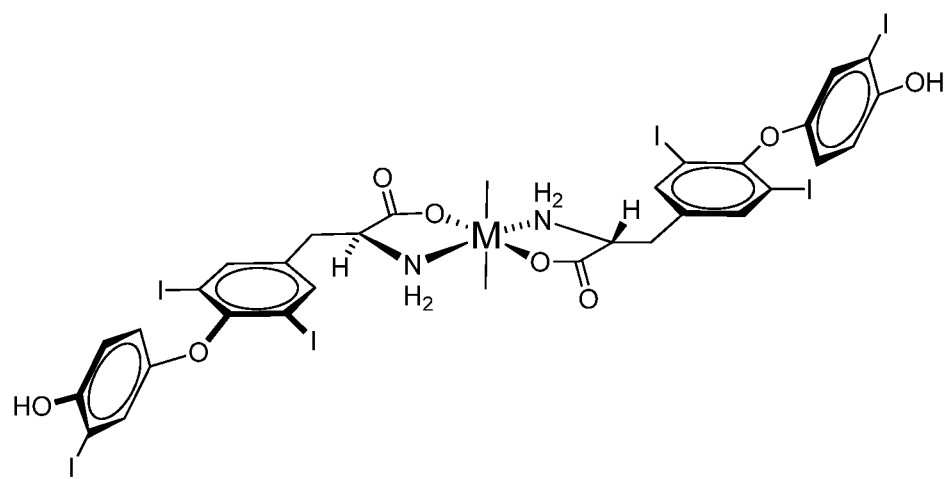
FIG. 3 is a coordination mode for discrete mononuclear T3 complexes. An octahedral geometry is shown for the metal center. Square planar geometries are also embodied for some of the metals studied.

The following paragraphs define in more detail the embodiments of the invention described herein. The following embodiments are not meant to limit the invention or narrow the scope thereof, as it will be readily apparent to one of ordinary skill in the art that suitable modifications and adaptations may be made without departing from the scope of the invention, embodiments, or specific aspects described herein. All patents and publications cited herein are incorporated by reference herein in their entirety.

For purposes of interpreting this specification, the following terms and definitions will apply and whenever appropriate, terms used in the singular will also include the plural and vice versa. In the event that any definition set forth below conflicts with any document incorporated herein by reference, the definition set forth below shall control.

The term "patient" refers to any subject including mammals and humans. The patient may have a disease or suspected of having a disease and as such is being treated with a drug. In some instances, the patient is a mammal, such as a dog, chicken, cat, horse, or primate. In some instances, the term "patient," as used herein, refers to a human (e.g., a man, a woman, or a child). In some instances, the term "patient," as used herein, refers to laboratory animal of an animal model study. The patient or subject may be of any age, sex, or combination thereof.

The terms "active ingredient," "active pharmaceutical ingredient," "bioactive agent," "biologically active moiety," or "therapeutic agent" as used herein refer to a pharmaceutical agent, active ingredient, compound, substance or drug, compositions, or mixtures thereof, that provide a pharmacological, often beneficial, effect. The active ingredient may be any pharmaceutically acceptable salt, hydrate, crystalline form or polymorph thereof.

The term "formulation" or "composition" as used herein refers to the active ingredient or drug in combination with pharmaceutically acceptable excipients.

The terms "dosage" or "dose" as used herein denote any form of the active ingredient formulation that contains an amount sufficient to produce a therapeutic effect with a single administration.

The term "ligand exchange" or "ligand exchange reaction" as used herein are intended to encompass all forms of ligand exchange reactions, including hydrolysis, where the exchanging ligand is water.

The term "controlled release" as used herein refers to a composition that releases an active ingredient at a slower rate than does an immediate release formulation under physiological conditions or in an in vitro test.

The term immediate release" as used herein refers to a composition that releases the majority of an active ingredient following administration (e.g., greater than 50% of the active ingredient).

The term "sustained release" as used herein refers to a composition that releases an active ingredient over an extended period of time, for example minutes, hours, or days, such that less than all the active ingredient is released initially. A sustained release rate may provide, for example, a release of a certain specified amount of a drug or active ingredient from a dosage form, over a certain period, under physiological conditions or in an in vitro test.

The term "treating" refers to administering a therapy in an amount, manner, or mode effective to improve a condition, symptom, or parameter associated with a disorder. In some embodiments, the compound described herein is used to treat a patient having a disease in need of treatment thereof.

As used herein, "a" or "an" means one or more unless otherwise specified.

In some embodiments is a supramolecular metal coordination complex according to formula I

wherein:
M is a metal atom;
D is a biologically active moiety that comprises at least two functional groups that are capable of coordinating to a divalent metal;
A is a second biologically active moiety or adjuvant;
W is H2O;
x is an integer from 1 to 10;
o is an integer from 1 to 10;
a ratio of p to x is from about 1/1000 to about 1000/1;
q is zero or an integer from 1 to 20; and
n is an integer greater than or equal to 2.

In one embodiment, A is a second biologically active moiety, which is any suitable active biologically active moiety that is further described herein. In another embodiment, A is a suitable adjuvant that is further described herein.

In another embodiment, x is 1. In another embodiment, x is 2. In another embodiment, x is 3. In another embodiment, x is 4. In another embodiment, x is 5. In another embodiment, x is 6. In another embodiment, x is 7. In another embodiment, x is 8. In another embodiment, x is 9. In another embodiment, x is 10.

In another embodiment, o is 1. In another embodiment, o is 2. In another embodiment, o is 3. In another embodiment, o is 4. In another embodiment, o is 5. In another embodiment, o is 6. In another embodiment, o is 7. In another embodiment, o is 8. In another embodiment, o is 9. In another embodiment, o is 10.

In another embodiment, p is 0. In another embodiment, p is an integer greater than or equal to 1. In another embodiment, p is 1. In another embodiment, p is 2. In another embodiment, p is 3. In another embodiment, p is 4. In another embodiment, p is 5. In another embodiment, p is 6. In another embodiment, p is 7. In another embodiment, p is 8. In another embodiment, p is 9. In another embodiment, p is 10.

In another embodiment, q is 0. In another embodiment, q is an integer greater than or equal to 1. In another embodiment, q is 1. In another embodiment, q is 2. In another embodiment, q is 3. In another embodiment, q is 4. In another embodiment, q is 5. In another embodiment, q is 6. In another embodiment, q is 7. In another embodiment, q is 8. In another embodiment, q is 9. In another embodiment, q is 10. In another embodiment, q is 11. In another embodiment, q is 12. In another embodiment, q is 13. In another embodiment, q is 14. In another embodiment, q is 15. In another embodiment, q is 16. In another embodiment, q is 17. In another embodiment, q is 18. In another embodiment, q is 19. In another embodiment, q is 20.

In another embodiment, n is an integer greater than or equal to 1. In another embodiment, n is an integer greater than or equal to 2. In another embodiment, n is an integer greater than or equal to 5. In another embodiment, n is an integer greater than or equal to 10. In another embodiment, n is an integer greater than or equal to 50. In another embodiment, n is an integer greater than or equal to 100. In another embodiment, n is an integer greater than or equal to 100. In another embodiment, n is an integer greater than or equal to 500. In another embodiment, n is an integer greater than or equal to 1000.

In another embodiment, a ratio of p to x is from about 1:750 to about 750:1. In another embodiment, a ratio of p to x is from about 1:500 to about 500:1. In another embodiment, a ratio of p to x is from about 1:100 to about 100:1. In another embodiment, a ratio of p to x is from about 1:10 to about 10:1. In another embodiment, a ratio of p to x is from about 1:5 to about 5:1. In another embodiment, a ratio of p to x is from about 1:1.

Another embodiment described herein are metal coordinated triiodothyronine (T3) complexes according to formula I. These complexes produce T3 plasma concentrations similar to the normal (euthroid) state with once daily dosing. The metallo-T3 complexes are designed to extend the transit time through the gastrointestinal tract where T3 molecules are gradually released from the metal complex through a ligand exchange reaction and absorbed into the blood stream. The ligand exchange process modulates the rate of delivery and thereby the rate of absorption.

This modulated absorption is accomplished by forming polymeric complexes composed of di- and trivalent metals ions with a polydentate dianion of T3. Although amino acids can bind to cations as a monodentate, bidentate, or tridentate ligand, the tridentate coordination mode is sterically unfavorable when it involves only the three ligand atoms of the amino acid group. In contrast, amongst the natural amino acids, Tyr and T3 can act as tridentate ligands via additional participation of the phenol group. The phenol group is a potential metal binding site and therefore can be involved in cation coordination. When the phenol group is deprotonated, it both influences coordination mode and favors formation of supramolecular vs. discrete structures. The stability of the former, and thus the hydrolysis kinetics, is controlled by choice of metal and the phenomenon of significant inter-T3 interactions as described below.

Figure 4:
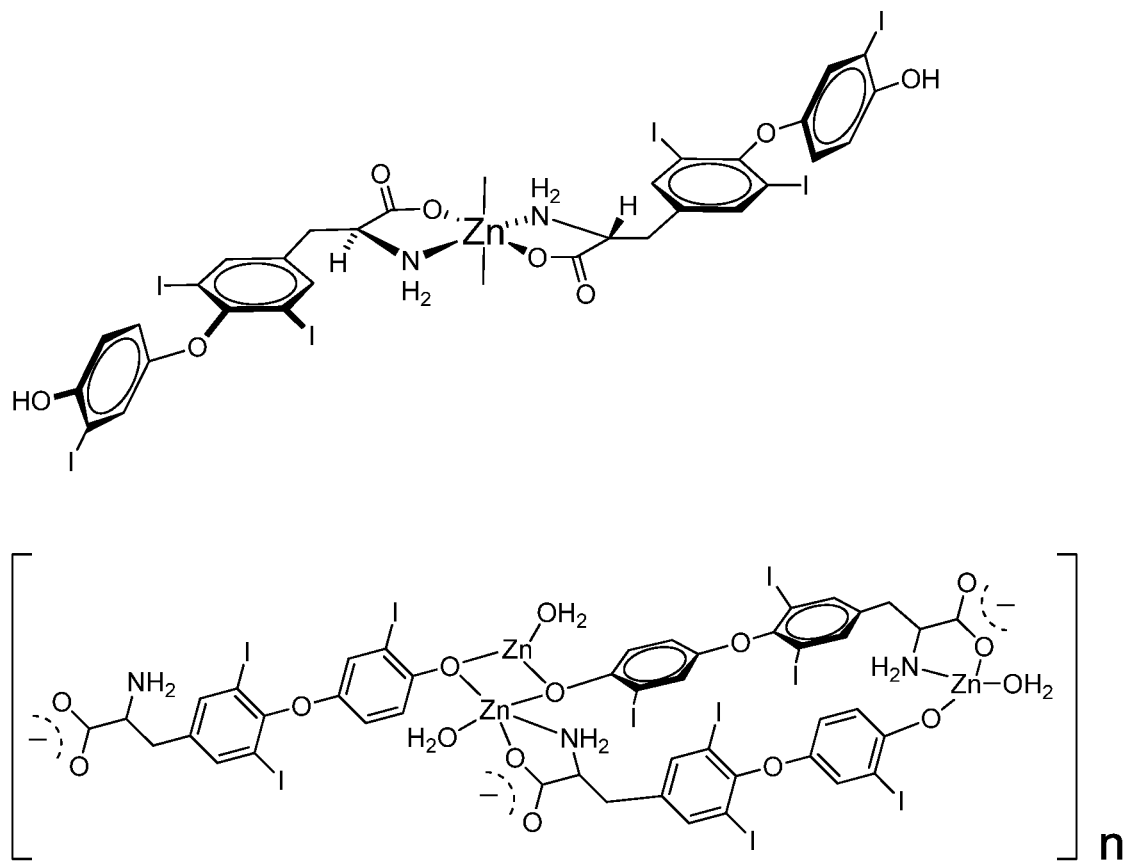
FIG. 4 is an example of discrete (top) vs. supramolecular (bottom) zinc complexes of T3.
Figure 5:
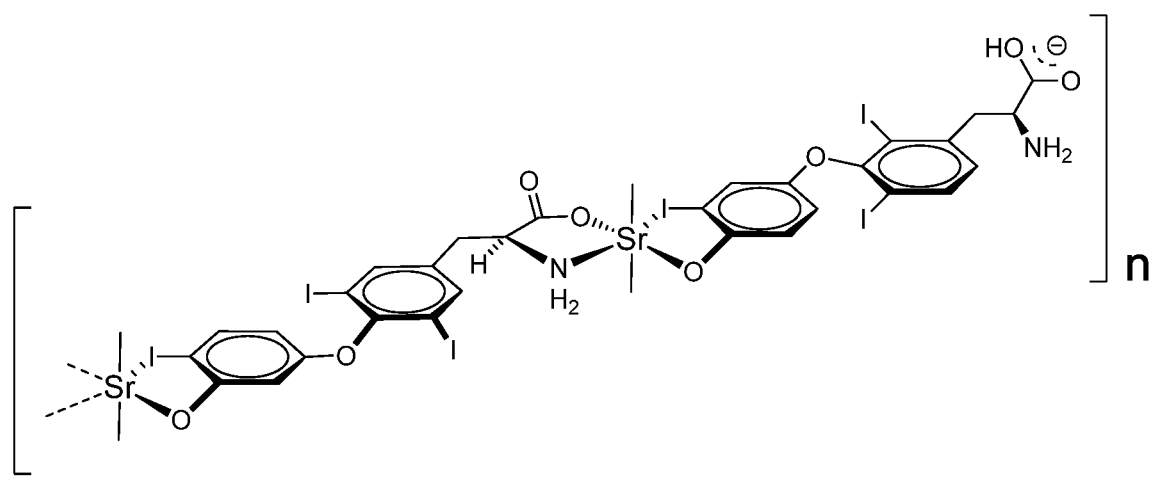
FIG. 5 is an illustration of a coordination mode highlighting Head-Tail/T3-T3 orientation, and secondary coordination bonding interactions between iodine and Sr, in the polynuclear complex. This is a theoretical repeating unit for the polynuclear complex. Although it is shown for a linear system, 2- and 3-dimensional motifs are possible. Also shown is an example of a metal-halogen bond between Sr and 13 of T3.
Figure 6:
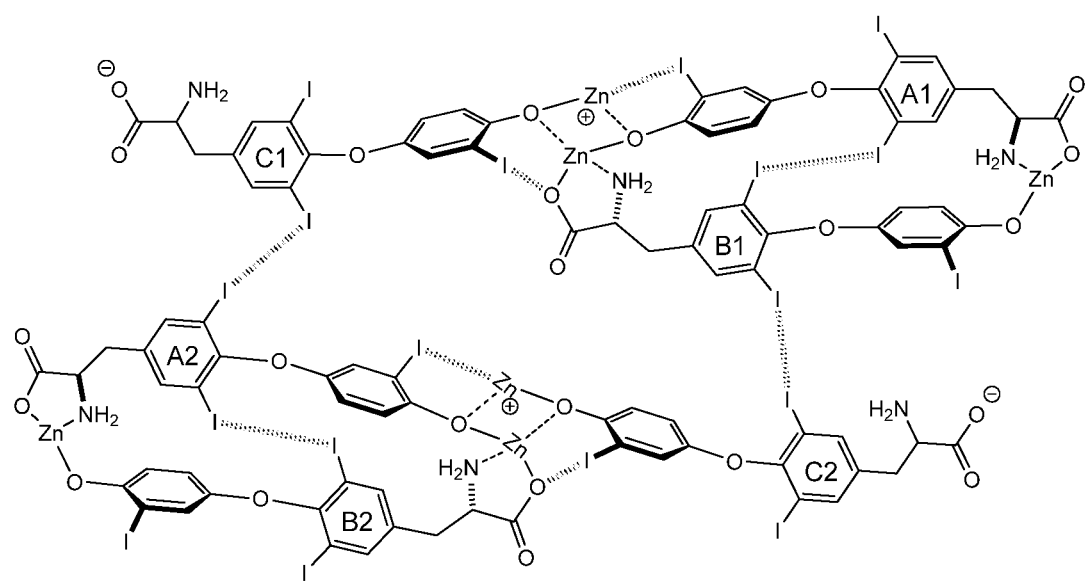
FIG. 6 is an illustration of strong bonding interactions (coordinate covalent bonds) between Zn and ligand donor atoms of $T3^{2-}$ are shown in black; Weak bonding interactions (halogen bonds) between iodine and X-bond acceptor atoms of $T3^{2-}$ are shown in dashed red. Both bonding modes contribute to polymer formation and stabilization. Two- and 3-D structures, including metal organic frameworks, are possible.

The phenol of T3 (pKa 8.94) can be deprotonated generating a dianionic ligand. Thus, another ligand atom is available for the coordination of cations. Consequently, these $T3^{-2}$ dianions are divalent, with negative charges at opposite ends, which allows connection of units to chains, and higher ordered 2- and 3-dimensional species. $T3^{-2}$ dianions act as bridging ligands via the functional groups at the α-carbon at the head of the molecule, and the phenolate oxygen at the tail (see FIGS. 4 & 5). This coordination motif has been observed for the amino acid tyrosine with various metals.

The formation constants of $s^2$-block metals with mono- and bidentate amino acid ligands are low, making them susceptible to hydrolysis in aqueous media. Coordination complexes of transition metals with monovalent species of T3 can yield polymeric structures through inter-molecular bonding between $M^{2+}(HT3^{-1})_2$ discrete subunits. However, the supramolecular bonding mechanisms in these cases involve non-covalent interactions such as relatively weak hydrogen bonding. They are more resistant to hydrolysis in aqueous media than s-block complexes, but at times, do not produce a sufficiently sustained release of T3 in vivo.

Without rejecting the monovalent $HT3^{-1}$ approach, a novel approach to preparing polymeric complexes of T3 suitable for controlled in vivo release of T3 was developed by producing a tridentate form of T3 capable of bonding with metal ions. This tridentate form of T3 ($T3^{2-}$) generated via the two ionizable functional groups (amino acid and phenol) can form two coordinate covalent bonds with a metal, resulting in 1-, 2-, and 3-D-supramolecular species. Complexes of this type, where the polymer is composed of covalently coordinated monomers, are superior to supramolecular compounds assembled via non-covalent interactions between discrete complexes to deliver orally delivered T3 in a controlled pharmacokinetic fashion.

It is, therefore, an embodiment of this invention that a new class of complex of the form $[M(T3)]_n$ has been made where M=$s^1$- and $s^2$-block elements; transition metals; p-block elements, including but not limited to Sn, Pb, and Bi; Actinides and Lanthanides; metal clusters, and other cationic species, and T3 is the dianion of triiodothyronine ($T3^{2-}$). It is a further embodiment of this invention that these supramolecular complexes of the form $[M(T3)]_n$ have superior mucoadhesive properties. It is a further embodiment of this invention that the mucoadhesive and ligand exchange properties inherent in the $[M(T3)]_n$ complexes translate into an SR formulation of T3 capable of producing euthyroid conditions in hypothyroid patients.

Basis of Mucoadhesion and Mucoadhesive Drug Delivery Systems

Mucoadhesion is the phenomenon by which two surfaces, one of which is mucus or a mucous membrane, and the other the surface of a drug or drug delivery system, are held together for extended periods of time by interfacial forces.

Over the past few decades, mucoadhesive drug delivery has been developed due to the ability of these dosage forms to adhere to a mucosal surface, enabling prolonged retention at the site of a drug's application, and providing a controlled rate of drug release for improved therapeutic outcome. (1) For adhesion to occur, molecules often bond across the mucus-adhesive interface; the strongest bonds arise from ionic, covalent, and hydrogen bonding. (2) Mucoadhesion results in slower transit time in the gut, which confers sustained period of absorption in the GI tract.

Mucoadhesives are generally macromolecules containing numerous hydrogen bond forming groups capable of interacting with the negatively charged mucosal surface. (Smart, 2005) The mucosal surface is enriched in glycoproteins and oligosaccharides, ligands with electron donating functionality. These include sialic acid, sialoglycoproteins, uronates, and amino acids such as histidine (imidazole), and cysteine (thiolate).

Controlled Release of Drugs Via Metal Coordination Complexes.

Not to be bound by a single approach, generally making a controlled release, orally delivered drug product via metal coordination of a drug ligand utilizes known principles of mucoadhesion and coordination chemistry. (Lawrance, 2010) For illustrative purposes only, consider the Metal Coordinated Pharmaceutical (MCP) as a prodrug. Then the process of modified drug release and absorption can be seen to involve three distinct processes: A) Mucoadhesion to an area of the GI tract, B) Controlled ligand exchange of drug from the MCP, followed by C) Absorption of the released reference drug.

I. Mucoadhesion of Metal Coordinated T3 Complexes.

Mucoadhesives are generally macromolecules containing numerous hydrogen bond forming groups capable of interacting with the negatively charged mucosal surface. The mucosal surface is enriched in glycoproteins and oligosaccharides, ligands with electron donating functionality. These include sialic acid, sialoglycoproteins, uronates, and amino acids such as histidine (imidazole), and cysteine (thiolate).

Metal Coordinated Pharmaceuticals have mucoadhesive properties when they (1) are polymeric or form clusters; or (2) interact with the mucosal membrane.

1. Coordination polymers, polymer networks and clusters are made from neutral or anionic ligands having at least two donor sites (i.e. multitopic ligands). These ligands coordinate to metal ions or aggregates having at least two acceptor sites, so that at least a one-dimensional arrangement is possible. Depending on the number of donor atoms and their orientation in the linker, and on the coordination number of the node, different one (1D)-, two (2D)- and three (3D)-dimensional constructs can be synthesized. Coordination polymers can also form when a ligand has multiple coordination sites that act as bridges between multiple metal centers. For example, tyrosine possesses three functional groups capable of forming metal coordination bonds; two sites of coordination are possible (amino acid and phenolate); and coordination polymers of tyrosine are known. T3 not only satisfies this requirement, but possesses the identical coordination motif (amino acid and phenol). T3, unlike tyrosine, can also form metal-halogen bonds introducing another mode of bonding which can contribute to supramolecular structures.

It is an embodiment of this invention that under certain conditions and/or with certain metals, insoluble polymeric metal coordinated complexes of T3 are produced. The insoluble nature of such metallo-T3 complexes provides a means for oral delivery of metal coordinated T3 (MC-T3) to the GI tract, where it is adsorbed and released via ligand exchange. Moreover, due to the multiplicity of binding sites imparted by supramolecular materials, supramolecular MC-T3 can exhibit very strong mucoadhesive properties. Thus, in some embodiments in accordance with the present teachings, the MC-T3 complex has a polymeric or supramolecular structure.

2. Mucoadhesion is a property of many metal complexes due to the interaction of the metal, which acts as a Lewis acid, with anionic components of the mucosa. Mucoadhesion depends on the metal, the structure of the complex, and the size and charge of the drug particles. Mucoadhesion prolongs the residence time of a drug in the GI tract. MC-T3 interacts with the mucosa by a variety of additional mechanisms, including, but not limited to: coordinate covalent bonding, hydrogen bonding, halogen bonding, metal-halogen bonding, electrostatic interactions, and particle size.

2a. Coordinate covalent bonding: Positively charged metal centers can bind to the mucous membrane by forming covalent coordinate bonds with ligands found on the mucosal surface. This is an additional, underexploited, mechanism for mucooadhesion between two surfaces. For example, bismuth subdopate (BSD), a bismuth-levodopa coordination polymer, demonstrated adhesion and a sustained release of levodopa in various animal models. T3 (amino acid and phenol) has similar coordination modes to levodopa (amino acid and catechol), and coordination complexes of T3 behave similarly. Although it was difficult to form polymeric complexes between T3 and bismuth (presumably due to steric hindrance between bismuth and iodine-3 of T3) complexes with a wide range of smaller metals are an embodiment of this invention. (Bismuth is the largest non-radioactive metal on the periodic table.) These metals also interact with the mucin ligands.

2b. Hydrogen bonding. Glycoproteins in general, including the mucosal glycoprotein layer possess hydrogen bond donors capable of bonding with hydrogen bond acceptors of T3 (O, N, I). Solid state crystal packing of thyroid hormones shows extensive H-bonding generally involving the amine group, 4'-OH group, carboxylic acid group and $H_2O$ of crystallization. These T3 moieties interact with the mucosa as an embodiment of this invention.

2c. Halogen bonding. The mucosa layer is composed of many halogen bond acceptors (O, N, S) capable of forming halogen bonds with the iodines of T3. (Mugesh, 2016) These interactions are called halogen bonding because the negative potential of one acceptor interacts with the positively charged σ-hole of a halogen atom. An interesting feature of the crystal packing of thyroid hormones is the I . . . I noncovalent interactions, where the halogen may act as both halogen bond acceptor and donor. Depending on the angular contacts of the halogen atoms involved in the interaction, two different kinds of X . . . X interactions have been proposed. Type II contacts are generally recognized by the perpendicular arrangements of the two C—X bonds, i.e., θ1=180° and θ2=90°. These interactions are called halogen bonding because the lateral negative potential of one halogen interacts with the positively charged σ-hole of the other halogen atom. For type I interactions, |θ1-θ2| should be in between 0° and 15°, whereas for type II interactions, |θ1-θ2| should be greater than 30°.

2d. Metal-halogen bonding: Metal-halogen bonding describes a non-covalent weak-bond (on the order of hydrogen bonding). The bond is formed between the positive charge on a metal interacting with the induced negative charge on a halogen. The positive charge on a halogen is highly localized in the area known as the sigma-hole. The rest of the atom has a net negative charge, due to the electronegativity of halogens. A metal-halogen bond would be expected to be strongest in molecular networks where the metal is not shielded by solvent molecules, i.e. a coordination complex. In a salt, water molecules are in the inner coordination sphere of the metal minimizing the strength of the metal-halogen bond.

2e. Electrostatic Interactions: Mucoadhesion is a consequence of interactions between the mucus layer on mucosa and mucoadhesive polymers. It is greatly dependent on mucus and polymer structure including their charges. It is also known that the glycosaminoglycan layer, which covers the intestinal mucosa surface, is highly negatively charged. Therefore, by measuring the zeta potential of polymer dispersions an insight into electrostatic interactions during mucoadhesion can be obtained. For example, the zeta potential (ζ) for coordination polymers, prepared between bismuth and levodopa was determined to be positive (ζ=+17 mV). When BSD was manually applied to bovine colonic tissue, the material adhered to the tissue after washing with simulated intestinal fluid. Uncoordinated levodopa was not retained. This experiment demonstrates the mucoadhesive properties inherent in a supramolecular metal coordination complex, which is an embodiment of this invention.

2f. Particle size: Generally, the smaller the particle, the greater the surface area of the particle relative to its mass and, therefore, the greater the mucoadhesion, It is an embodiment of this invention that all of the bond types described are strengthened by the clustering of the T3 molecules brought about by virtue of metal coordination. Many of these same interactions are responsible for the formation of higher ordered structures when they occur between MC-T3 molecules. It is a further embodiment of this invention that the increased strength of these bonds minimize solubility. It is a further embodiment of invention that low solubility combined with the enhanced points of attachment between the polymeric metal T3 complex and the glucosa glycoprotein layer impart unique and unexpected mucoadhesive properties to the polymeric metal T3 complex. Non-covalent bonding interactions between MC-T3 molecules and biological mucosa are responsible for the mucoadhesive properties of these materials. The more binding sites between the molecules and the mucosa lining, the greater the mucoadhesion. Thus polymeric structures, such as what is embodied in this invention, have stronger mucoadhesive properties than their discrete mononuclear congeners. It is an embodiment of this invention that mucoadhesion and formation of larger structures have a major impact on T3 absorption and the rate of absorption when the MC-T3 compound is delivered to the gut.

II. Controlled Drug Release from Metal Coordinated T3 Complexes.

The general approach to controlled drug release via MCPs is to utilize known principles of coordination chemistry to modify the rate of hydrolysis (release) of the drug ligand from the coordination matrix. Hydrolysis is dependent on many factors including:

1. Thermodynamic stability of the complex
2. pH
3. Endogenous ligands

1. Thermodynamic Stability of T3 Coordination Complexes.

T3 is an amino acid. Amino acids offer a great deal of flexibility as ligands, as each molecule possesses at least three highly electronegative atoms (two oxygen atoms in the carboxylate group plus one nitrogen atom in the amino group) which can act as ligand donor atoms. This allows for coordination of cations with different chemical properties (such as charge or ionic radius). Several coordination modes with metals are known. Amino acids can act as monodentate, bidentate, tridentate, and bridging ligands. As a bridging ligand, they can bond via one bridging atom (denoted as O, O) or two different bridging atoms (denoted as O, N or O, OO).

Amino acids in general form bidentate coordination compounds utilizing the (O, N) donor atom set. It is an embodiment of this invention that the metals used to form supramolecular coordination complexes with the bidentate $T3^{2-}$ ligand include $s^1$- and $s^2$-block elements; transition metals, p-block metals, including Sn and Bi; and the lanthanides and actinides.

The range of different connectivities within the coordination polyhedra of the metal cations is considerable. Discrete units are frequent, e.g. mono-, di-, tri-nuclear complexes, etc. In addition, the coordination polyhedron of the metal plus surrounding ligands can form a chemical building block from which higher ordered structures arise. These units are comprised of discrete coordination complexes, which can assemble into infinite coordinate covalent structures such as one-dimensional chains, two-dimensional layers, or three-dimensional frameworks.

Assembly of these metal coordinated amino acid building blocks into higher ordered structures, including polymeric complexes, is controlled largely by non-covalent bonding interactions between discrete complexes. Among these are hydrogen- and halogen-bonding, metal-halogen bonding, aromatic π-π interaction, and metal-aromatic ring interactions.

Triiodothyronine has a similar coordiphore to L-tyrosine. For L-tyrosinates, several complexes have been reported, all of which comprise divalent cations in combination with two monovalent $Tyr^{-1}$ anions. Most species comprise isolated units, as in the nickel and the palladium complexes, although bis-(L-tyrosinato)-copper has a chain structure.

Illustrative examples of a one-dimensional coordination polymeric structure based on discrete coordination complexes as building blocks exist in $\{[Zn(tyr)_2(H_2O)]H_2O\}_n$ and $[Cu(tyr)_2]_n$. Accordingly, tyrosine acts as a bridging ligand. In the case of the Zn example, the coordination polymer is created as an unstranded chain with trans coordination of the carboxylate group. In contrast to the unstranded 1D polymeric structure of the Zn-complex, $[Cu(tyr)_2]_n$ has a lefthanded helical arrangement. The most important reason for the unstranded structure formation of Zn-Tyr and the helical structure of Cu-Tyr is a different stereo geometry of the bridging carboxylate group in the coordination sphere of the $Zn^{2+}$ and $Cu^{2+}$ ions. A trans coordination results in the unstranded chain, whereas the cis coordination facilitates the helical structure.

Studies of L-tyrosinate anion interaction with metal ions lead to the understanding of the complex formation and the stability of its complexes in the solid state and in solvents. The formation of complexes is controlled by solution acidities, which is related to the pKa values (2.2 for COOH and 9.1 for $NH_3^+$ groups). The most typical coordination mode of L-tyrosine is via the N amino and one of the 0 atoms of the carboxylate group, which can be accompanied by the μ-bridging mode of the carboxylate group. The diversity of the binding modes of these groups generate monomeric, dimeric and metal-organic frameworks (MOFs). Interestingly, phenolate oxygen atoms have also been engaged in coordination to the metals ions by applying synthesis under solvothermal conditions with pH 9-10 for the deprotonation of the phenoxy group.

The compounds described in this invention may constitute Metal Organic Materials (MOMs) and/or Metal Organic Frameworks (MOFs). It is further embodiment of this invention that inherent in these MOM's and/or MOF's many mixed-ligand complexes of T3 with structurally similar molecules such as tyrosine can be made. Mixed ligand, or ternary complexes are complexes in which the metal ion has two or more types of ligands in its coordination sphere. These mixed ligand compounds T3 from a metal organic material, composed of a mixture of T3 and tyrosine (x/y), will have a release that is further delayed and controlled by the ratio of T3 (x=1) to ligand (y=1 to ∞).

The known chemistry of amino acid metal complexes, and in vitro dissolution studies of numerous synthesized MCPs, indicate that ligand hydrolysis is generally biphasic with respect to pH. In the lower pH ranges of the stomach, hydrolysis is rapid. Because the pH is highly variable (pH=1-5) depending on fed/fasted state, release kinetics are also variable. In the duodenum however, the pH is higher (>5.5) and fluctuates minimally with fed/fasted state. Drug release is slower and less variable. Delivery to the stomach (gel caps) or duodenum (Eudragit®-coated capsules) allows for control of pH at the site of drug release. At high pH (>10) hydrolysis also occurs. 3. Endogenous Ligands:

The presence of endogenous ligands, which compete for coordination also affects hydrolysis rate. Competing ligands in the GI tract include HCl (stomach), bile acids and carbonate buffers (upper intestines). The theoretical schematic of FIG. (1) illustrates many of these factors.

It is a further embodiment of this invention that drugs that possess two functional groups capable of coordinating to a divalent metal (i.e. bidentate) can form supramolecular structures as described in this document. Additional and non-limiting examples of drugs that are bidentate, and therefore, can form supramolecular complexes with divalent or multivalent metals are amoxicillin, cefotetan, furosemide, methotrexate, tetracycline and valsartan (see FIGS. 8-13).

Drugs such as valsartan and other tetrazole derivative that contains acid (pKa=4.73) and carboxylic (pKa=3.9) groups making the compound soluble in the neutral pH range are candidates for supramolecular metal coordination complexes described herein. Owing to these pKa values of the compound, valsartan exists as solution at physiological pH values as the undissociated acid, the mono-anion and the di-anion. On increasing the pH from 4 to 6 the solubility of valsartan increases by a factor of about 1000, but it favors the anionic form and decreases lipophilicity, hence the rate of absorption of valsartan is influenced by intestinal pH along the (GI)tract. In vitro dissolution is complete and rapid at pH 5.0 and above. As valsartan has pH dependent solubility it belongs to a special case in a proposed general classification system that categorizes drugs with respect to their biopharmaceutical and absorption properties. In the biopharmaceutical classification system, valsartan has been classified as Class III drug with low permeability, poor metabolism and high solubility. The pKa of Valsartan varies with the percentage of acetonitrile in ACN:water mixtures, with 60% ACN, pKa of carboxyl group is 5.321 and that of tetrazole is 6.189 with 55% ACN, pKa of carboxyl group is 5.143 and tetrazole group has pKa of 6.163. Under the influence of 50% ACN pKa of carboxyl group is 4.982 and that of tetrazole is 6.6130. Valsartan has bioavailability of about 25% due to its acidic nature. Being acidic in nature it is poorly soluble in the acidic environment of GIT and is absorbed from the upper part of GIT that is acidic in nature and Valsartan is 0.18 g/L soluble in water at 25° C. In a buffered solution a dianion salt is formed due to which its solubility is increased. In phosphate buffer (pH 8.0), valsartan is 16.8 g/L soluble at 25° C.

Quinolones represent another exemplary class of compounds, which may be used to form a supramolecular metal coordination complex described here. For example, the piperazinium group is deprotonated at pKa1 leaving a neutral amine. Although not a dianion, these compounds can still form coordination polymers through bonding of the neutral amine N and carboxylate O with transition metals. Not to be constrained by the above examples, the following drugs are also bidentate and can form supramolecular structures with divalent or multivalent metals, and therefore are also, another embodiment of this invention, which are provided in table 1 below.

TABLE 1

| Compound | pKa 1 | pKa 2 | pKa 3 |
|---|---|---|---|
| Tetracyclines | | | |
| Chlortetracycline | 3.33 | 7.55 | 9.33 |
| Demeclocycline | 3.37 | 7.36 | 9.44 |
| Doxycycline | 3.02 | 7.97 | 9.15 |
| Meclocycline | 4.05 | 6.87 | 9.59 |
| Oxytetracycline | 3.22 | 7.46 | 8.94 |
| Tetracycline | 3.32 | 7.78 | 9.58 |
| Quinolones | | | |
| Ciprofloxacin | 6.42 | 8.29 | |
| Danofloxacin | 6.07 | 8.56 | |
| Difloxacin | 5.66 | 7.24 | |
| Enoxacin | 6.00 | 8.50 | |
| Enrofloxacin | 3.85 | 6.19 | |
| Flerofloxacin | 5.46 | 8.00 | |
| Lomefloxacin | 5.00 | 6.25 | 9.00 |
| Marbofloxacin | 5.69 | 8.02 | |
| Norfloxacine | 6.22 | 8.38 | |
| Pefloxacin | 6.21 | 7.87 | |
| Pipemidic acid | 5.42 | 8.18 | |
| Ofloxacin | 6.22 | 7.81 | |
| Sarafloxacin | 5.62 | 8.18 | |
| Other Drugs | | | |
| Amoxicillin | 6.71 | 9.41 | |
| Cefotetan | ca. 2 | ca. 3 | |
| Furosemide | 3.8 | 7.5 | |
| Methotrexate | 4.8 | 5.6 | |
| Valsartan | 3.9 | 4.7 | |

EXAMPLES

Example 1

Preparation of $Zn(HT3)_2$. Bis-T3 Zinc. Na(HT3) (250 mg, 0.371 mmol) was added to a 50 mL round bottom flask and dissolved in methanol (35 mL). A solution of $ZnCl_2$ in methanol (25.2 mg, 0.185 mmol, Note 1) was added dropwise (200 μL over 8 minutes). A precipitate formed immediately. The reaction was stirred 19 hours at room temperature. The precipitate was filtered without vacuum; washed with methanol (2×10 mL) and dried under vacuum (RT, 0.5 torr) to afford a colorless solid. Yield 189.1 mg (0.139 mmol based on putative $Zn(HT3)_2$, 1365.4 g/mol); 37%.

Note 1: The methanolic $ZnCl_2$ solution was prepared by concentrating a THF solution of $ZnCl_2$ (0.7 M, 265 μL, 0.185 mmol) in a 2 dram vial and adding methanol (5 mL).

Note 2: $H_2T3$ and NaHT3 are obtained from Aldrich and used without further purification. $H_2T3$ assay: Assay for $H_2T3$ (HPLC) is 92.2% (theoretical for $Zn(HT3)_2$-MeOH is 93.1%). C, H, N, Zn Analysis: Galbraith, best fit using Jasper. For $Zn(HT3)_2$-MeOH observed (theory) C, 26.06 (26.65); H, 1.83 (1.88); N, 1.96 (2.00); Zn 4.51 (4.68). $^1$H NMR: ($d_6$-DMSO) Compound is soluble (5 mg/mL). δ 7.84 (s; 2H), 7.03 (d; J=4.0 Hz; 1H), 6.81 (d; J=8.0 Hz; 1H), 6.62 (dd; J=4.0 Hz, 8.0 Hz; 1H), 3.51 (br s; 1H), 3.23 (br m; 1H), 2.66 (br m; 1H Example 2

Preparation of $[Zn(T3)(H_2O)]_n$. Poly-Zinc-T3, a putative poly-nuclear complex. $H_2T3$ (200 mg, 307 μmol) was weighed into a 50 mL round bottom flask and suspended in methanol (20 mL). 1 M aq NaOH (615 μL, 615 μmol) was added dropwise by pipette and stirred until all T3 dissolved (5 min). $ZnCl_2$ in MeOH (5.00 mL, 308 μmol; see Note 1) was added dropwise with stirring to the $Na_2T3$ solution (200 μL at a time over 8 min). A white precipitate formed and the reaction was stirred 19 hours at room temperature. The precipitate was filtered without vacuum, washed with methanol (2×10 mL), and dried in the vac oven (RT, 0.5 torr). Yield 207 mg (283 μmol, 92.2% based on $[Zn(T3)(H_2O)]_n$, 732.4 g/mol).

Note 1: A methanolic solution of $ZnCl_2$ (61.6 mM) was prepared by adding 440 μL (308 μmol) of 0.7 M $ZnCl_2$ in THF to a 2 dram vial; drying under nitrogen; then redissolving in 5 mL of methanol. Note 2: The compound was not visibly soluble in MeOH, DMSO, or $H_2O$. The solubility of $Na_2T3$ in MeOH is greater than 50.0 mg/mL (71.9 mM; 695 g/mol). The methanolic solubility of $ZnCl_2$ is greater than 8.40 mg/mL (61.6 mM; 136.4 g/mol). $H_2T3$ assay: Assay for $H_2T3$ (HPLC) is 87.3% (theoretical for $Zn(T3)(H_2O)$ is 88.6%). C, H, N, Zn Analysis: Galbraith, best fit using Jasper. For $Zn(T3)(H_2O)$, observed (theory): C, 24.41 (24.60); H, 1.45 (1.65); N, 1.79 (1.91); Zn 8.20 (8.93).

Example 3

Preparation of $[Zn_6(T3)(tyr)_5]_n$. Poly-(Hexazinc-T3-pentatyrosine). $H_2T3$ (250 mg, 384 μmol) and $H_2$tyr (tyrosine, 348.4 mg, 1923 μmol) were weighed into a 200 mL round bottom flask and suspended in methanol (100 mL). The total amount of ligand ($H_2T3+H_2$tyr) was 2307 μmol, and the ratio of $H_2T3/H_2$tyr was 1/5. 1 M methanolic KOH (4615 μL, 4615 μmol) was added dropwise by pipette and stirred until all solid dissolved (30 min). $ZnCl_2$ in MeOH (Note 1, 20.0 mL, 2307 μmol; see Note 1) was added dropwise by addition funnel over 15 min. A white precipitate formed and the reaction was stirred 19 hours at room temperature. The precipitate was filtered without vacuum, washed with methanol (2×20 mL), and dried under vacuum (RT, 0.5 torr). Yield 476 mg (283 μmol, 64.3% based on $[Zn_6(T3)(tyr)_5]_n$ (1937.4 g/mol).

Note: The methanolic $ZnCl_2$ solution was prepared by concentrating a THF solution of $ZnCl_2$ (0.7 M, 3296 μL, 2307 μmol) in a vial and adding methanol (20.0 mL). Zinc content: The zinc content by the Hach titration method is 8.95% (theoretical for $Zn(T3)(H_2O)$ is 8.93%). $^1$H NMR: ($d_6$-DMSO, $D_2O$, $CDCl_3$, $CD_3OD$) Compound is insoluble.

Example 4

Preparation of $[Cu(T3)(H_2O)]_n$. Poly-Copper-T3. $H_2T3$ (201 mg, 0.308 mmol) was weighed into a 50 mL round bottom flask and suspended in methanol (20 mL). 1 M aq NaOH (615 μL, 615 μmol) was added dropwise by pipette and stirred until all T3 dissolved (5 min). $Cu(ClO_4)_2 \cdot 6H_2O$ in MeOH (371 mg, 0.308 mmol, 4 mL MeOH) was added dropwise with stirring to the $Na_2T3$ solution (200 μL at a time over 8 min). A white precipitate formed and the reaction was stirred 19 hours at room temperature. The precipitate was filtered without vacuum; washed with methanol (10 mL), then $H_2O$ (10 mL); and dried under vacuum (RT, 0.5 torr). Yield 152 mg (72%).

Note 1: It is important to use the Na-salt of T3, either as the commercial salt (NaHT3) or generated in situ via the reaction of $H_2T3$ and NaOH as above. Other Na-bases have not been investigated (e.g. $NaOCH_3$/MeOH, etc.). K bases do not give satisfactory results. $H_2T3$ assay: Assay for $H_2T3$ (HPLC) is 92.6% (theoretical for Cu(T3), MW 712.51 g/mol, is 91.1%). $^1H$ NMR: ($d_6$-DMSO, $D_2O$, $CDCl_3$, $CD_3OD$) Compound is insoluble.

Example 5

Preparation of $[Mg(T3)-2H_2O]_n$. Poly-Magnesium T3. $H_2T3$ (200 mg, 307 μmol) was weighed into a 50 mL round bottom flask and suspended in anhydrous methanol (10 mL). Methanolic KOH (1.0 M, 615 μL, 615 μmol) was added dropwise by pipette and stirred until all T3 dissolved (5 min). The $K_2T3$ was stirred an additional 15 mins. A solution of $MgCl_2$ in MeOH (29.17 mg, 307 μmol; 15 mL) was added dropwise with stirring to the $Na_2T3$ solution (200 μL at a time over 5 min). A white precipitate formed immediately and the reaction was stirred 18 hours at room temperature. The precipitate was filtered, washed with methanol (2×10 mL), and dried in the vac oven (RT, 0.5 torr). Yield was 180.6 mg (255 μmol, 83%) based on $Mg(T3)-2(H_2O)$, (709.3 g/mol). The compound was not visibly soluble in MeOH, DMSO, or $H_2O$.

The solubility of $Na_2T3$ in MeOH is greater than 10.7 mg/mL (15.4 mM; 695 g/mol). The methanolic solubility of $SrCl_2-6H_2O$ is >5.4 mg/mL (76.9 mM; 266.5 g/mol). Magnesium content: The magnesium content by the Hach titration method is 3.9% (theoretical for $Mg(T3)-2(H_2O)$, 709.3 g/mol, is 3.4%). C, H, N, Mg Analysis: Galbraith, best fit using Jasper. For $Mg(T3)-2H_2O-0.35H_2O$: observed (theory) C, 24.89 (25.18); H, 1.79 (2.07); N, 1.91 (1.96); Mg 3.77 (3.40).

$^1H$ NMR: ($d_6$-DMSO, $D_2O$, $CDCl_3$, $CD_3OD$) Compound is insoluble.

Example 6

$[Ca(T3)-2H_2O]_n$. Poly-Calcium-T3. $H_2T3$ (200 mg, 307 μmol) was weighed into a 50 mL round bottom flask and suspended in anhydrous methanol (10 mL). Methanolic KOH (1.0 M, 615 μL, 615 μmol) was added dropwise by pipette and stirred until all T3 dissolved (5 min). The $K_2T3$ was stirred an additional 15 mins. A solution of $CaCl_2-2H_2O$ in MeOH (33.9 mg, 307 μmol; 5 mL) was added dropwise with stirring to the $K_2T3$ solution (200 μL at a time over 5 min). A white precipitate formed immediately, and the reaction was stirred 18 hours at room temperature. The precipitate was filtered, washed with methanol (2×10 mL), and dried in the vac oven (RT, 0.5 torr). Yield was 140.7 mg (185 μmol, 60%) based on $Ca(T3)-2(H_2O)$, (761.1 g/mol).

The compound was not visibly soluble in MeOH, DMSO, or $H_2O$. The solubility of $K_2T3$ in MeOH is greater than 50 mg/mL (68.9 mM; 727 g/mol). The methanolic solubility of $CaCl_2)-2H_2O$ is >6.8 mg/mL (61.4 mM; 147.0 g/mol). Calcium content: The calcium content by the Hach titration method is 5.3% (theoretical for $Ca(T3)-4(H_2O)$, 761.1 g/mol, is 5.3%). $H_2T3$ assay: Assay for $H_2T3$ (HPLC) is 84.0% (theoretical for $Ca(T3)-4(H_2O)$, 761.1 g/mol, is 85.3%). $^1H$ NMR: ($d_6$-DMSO, $D_2O$, $CDCl_3$, $CD_3OD$) Compound is insoluble.

Example 7

$[Sr(T3)-4H_2O]_n$. Poly-Strontium-T3. $H_2T3$ (200 mg, 307 μmol) was weighed into a 50 mL round bottom flask and suspended in anhydrous methanol (10 mL). Methanolic KOH (1.0 M, 615 μL, 615 μmol) was added dropwise by pipette and stirred until all T3 dissolved (5 min). The $K_2T3$ was stirred an additional 15 mins. A solution of $SrCl_2-6H_2O$ in MeOH (81.7 mg, 307 μmol; 5 mL) was added dropwise with stirring to the $K_2T3$ solution (200 μL at a time over 5 min). A white precipitate formed immediately, and the reaction was stirred 18 hours at room temperature. The precipitate was filtered, washed with methanol (2×10 mL), and dried in the vac oven (RT, 0.5 torr). Yield was 217 mg (268 μmol, 87%) based on $Sr(T3)-4(H_2O)$, (808.6 g/mol).

The compound was not visibly soluble in MeOH, DMSO, or $H_2O$. The solubility of $K_2T3$ in MeOH is greater than 50 mg/mL (68.9 mM; 727 g/mol). The methanolic solubility of $SrCl_2-6H_2O$ is >16.3 mg/mL (61.2 mM; 266.5 g/mol).

Strontium content: The strontium content by the Hach titration method is 10.8% (theoretical for $Sr(T3)-4(H_2O)$, 808.6 g/mol, is 10.8%). $H_2T3$ assay: Assay for $H_2T3$ (HPLC) is 79.6% (theoretical for $Sr(T3)-4(H_2O)$, 808.6 g/mol, is 80.3%). C, H, N, Sr Analysis: Galbraith, best fit using Jasper. For $Sr(T3)-1.3H_2O$: observed (theory) C, 23.80 (23.71); H, 1.66 (1.67); N, 1.74 (1.84); Sr 10.19 (11.53). For $Sr(T3)-4H_2O$: Sr 10.19 (10.84). $^1H$ NMR: ($d_6$-DMSO, $D_2O$, $CDCl_3$, $CD_3OD$) Compound is insoluble.

Example 8

Preparation of $Na_2(T3)$. Disodium-T3. $H_2T3$ (200 mg, 307 μmol) was weighed into a 50 mL round bottom flask and suspended in methanol (20 mL). 1 M aq NaOH (615 μL, 615 μmol) was added dropwise by pipette and stirred until all T3 dissolved (5 min). Stirring was continued for an additional 30 min, and solvent was removed under reduced pressure leaving a white solid. This was dried in the vac oven (RT, 0.5 torr).

Example 9

Preparation of $K_2(T3)$. Dipotassium T3. $H_2T3$ (250 mg, 384 μmol) 1M methanolic KOH (768 μL, 768 μmol) was added dropwise by pipette and stirred until all solid dissolved (30 min). Stirring was continued for an additional 30 min, and solvent was removed under reduced pressure leaving a white solid. This was dried in the vac oven (RT, 0.5 torr).

Example 10

In vivo studies. Plasma concentration vs time curves (plasma profiles) were obtained using deuterium labelled liothyronine compounds in male Sprague Dawley rats after oral administration. Labeled liothyronine was used to differentiate administered drug from endogenous hormone. The deuterated material ($H_2T3-d_3$) was used to prepare metal coordinated T3-$d_3$ samples as in Examples 1 and 2: $Zn(HT3-d_3)_2$; and $[Zn(T3-d_3)_n]$. $Na(HT3-d_3)$ was prepared as simulated Cytomel to allow for comparison with metal coordinated liothyronine test compounds.

The test articles were dosed orally (PO) into male Sprague-Dawley rats. Blood samples were drawn from the jugular vein catheter (JVC) and plasma samples were generated for analysis. None of the animals exhibited adverse reactions to the study treatment. Sprague-Dawley male rats were obtained from Hilltop Lab Animals, Scottdale, Pa. 15683; surgical catheters were implanted by ASLP. Deuterated T3 ($H_2T3$-$d_3$) was prepared by a modification of the procedure of Hashimoto. (Makoto Hashimoto, 2013)

The dosing capsules (Torpac, size 9 rat capsules) were prepared by Synthonics. To simulate Cytomel®, Na(HT3-$d_3$) was not coated; while the complexes were coated with Eudragit L100-55 to avoid premature acid hydrolysis of the metal coordinated complexes in the stomach, and release their contents in the duodenum.

Rats ranged in weight from 345 to 354 g. Animals were supplied with water and a commercial rodent diet ad libitum prior to study initiation. Food was withheld from the animals for a minimum of twelve hours before the study and during the study, until four hours post-dose, when food was returned. Water was supplied ad libitum. Animals were dosed PO at time 0 on the appropriate day. The animals were euthanized with carbon dioxide ($CO_2$) after the final blood samples were collected.

Blood samples (~400 μL) were collected via JVC and placed into chilled blood collection tubes containing sodium heparin as the anticoagulant, and kept on ice until centrifugation. Blood samples were centrifuged at a temperature of 2 to 8° C., at 3,000 g, for 5 minutes. Plasma samples were collected after centrifugation. Plasma samples were immediately frozen on dry ice and stored at −60° C. to −80° C. until shipped to Sponsor for analysis. Plasma samples were shipped frozen on dry ice to Synthonics where they analyzed to determine d-T3 concentrations using a validated LC-MS-MS method. The study design is shown in Table 2 and the resulting pharmacokinetic parameters are shown in Table 3.

TABLE 2

In vivo Study Design:

| Group # | Test Article | Dosing Route | Animals N = | Dose (μg/mL) | Capsule Coating | Sampling Time Points |
|---|---|---|---|---|---|---|
| 1 | Na(HT3-$d_3$) | PO | 8 | 12 | Gel cap, uncoated | 30, 60, 90 mins 2, 4, 6, 10, 12 hours |
| 2 | Zn(HT3-d)$_2$ | PO | 8 | 12 | Eudragit L100-55 | 30, 60, 90 mins 2, 4, 6, 10, 12 hours |
| 3 | [Zn(T3-d)]$_n$ | PO | 8 | 12 | Eudragit L100-55 | 30, 60, 90 mins 2, 4, 6, 10, 12 hours |

Key Pharmacokinetic (PK) Parameters

TABLE 3

Key Pharmacokinetic (PK) Parameters

| Test Drug | $C_{max}$ +/− SD (ng/mL) | $t_{max}$ (hours) |
|---|---|---|
| Na(HT3-$d_3$) | 1.14 (0.82) | 4 |
| Zn(d-HT3)$_2$ | 0.64 (0.31) | 4 |
| [Zn(d-T3)]$_n$ | 0.95 (1.08) | 6 |

Figure 7:
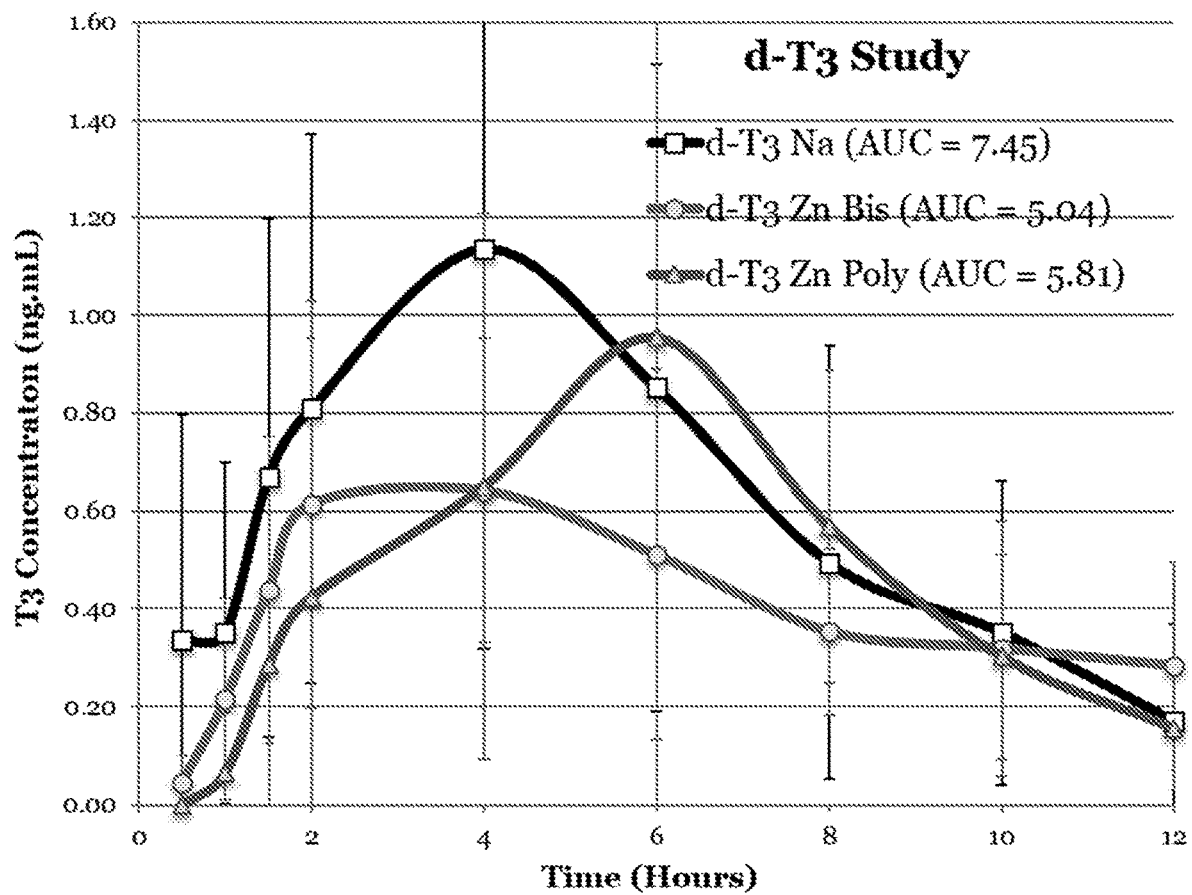
FIG. 7 Is a graph showing the concentration of T3 over time after oral administration of d-T3 Zn Bis $((HT3-d_3)_2)$, d-T3 Zn Poly $([Zn(T3-d_3)]_n)$, and d-T3 Na $(Na(HT3-d_3))$ to male Sprague Dawley rats.
Figure 8:
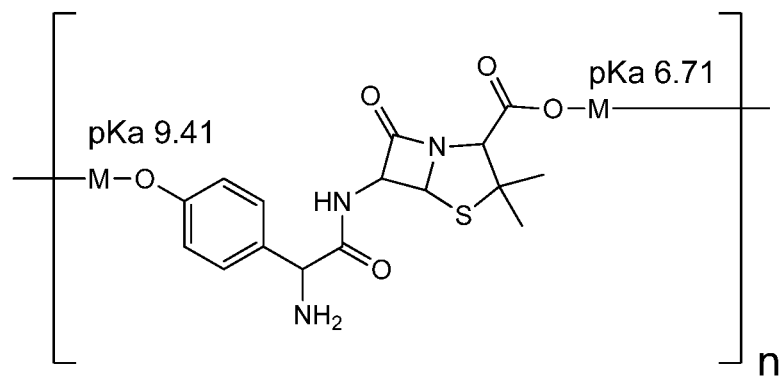
FIG. 8 is a theoretical structure showing a coordination motif between amoxicillin and a divalent metal cation leading to the repeating unit of a coordination polymer. The charge on amoxicillin is −2, obtained by deprotonation of two acidic groups. The $pK_a$ of the carboxylic acid is 6.71; the $pK_a$ of the phenol is 9.41. The $pK_a$ values may be shifted as much as 2 log units due to the chelation effect. This arises by the metal cation stabilizing the incipient negative charge during deprotonation.
Figure 9:
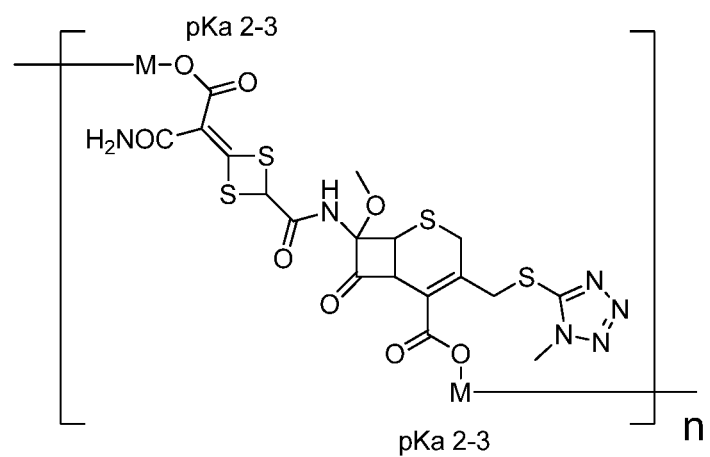
FIG. 9 is a theoretical structure showing a coordination motif between the dianion of cefotetan and a divalent metal cation leading to the repeating unit of a coordination polymer. The charge on cefotetan is −2, obtained by deprotonation of two carboxylic acid groups. The $pK_a$ of the carboxylic acids is estimated as 2-3.
Figure 10:
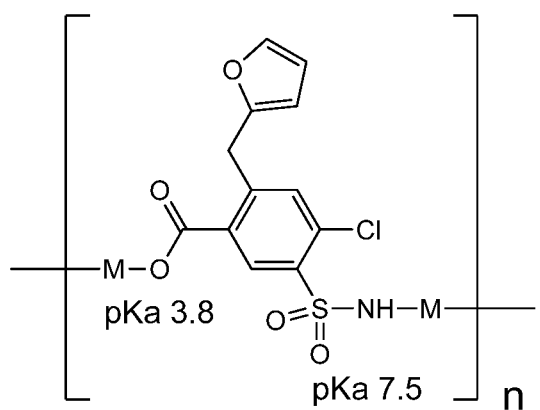
FIG. 10 is a theoretical structure showing a coordination motif between the dianion of furosemide and a divalent metal cation leading to the repeating unit of a coordination polymer. The $pK_a$ of the carboxylic acids is 3.8; the $pK_a$ of the sulfonamide is 7.5.
Figure 11:
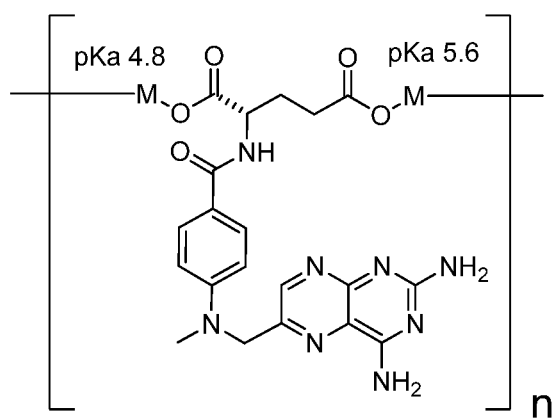
FIG. 11 is a theoretical structure showing a coordination motif between the dianion of methotrexate and a divalent metal cation leading to the repeating unit of a coordination polymer. The $pK_a$ of the carboxylic acids are 4.8 and 5.6.
Figure 12:
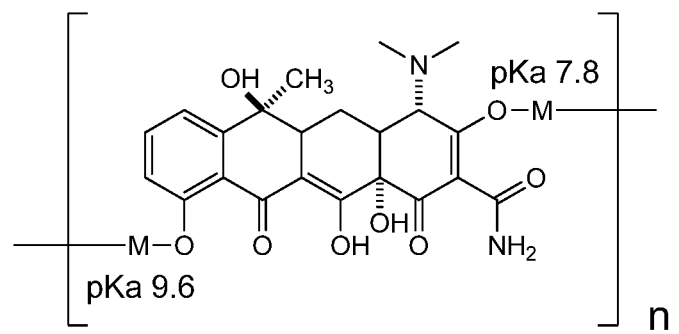
FIG. 12 is a theoretical structure showing a coordination motif between the dianion of tetracycline and a divalent metal cation leading to the repeating unit of a coordination polymer. The $pK_a$ of enol of ring A is 7.8; the $pK_a$ of the phenol is 9.6.
Figure 13:
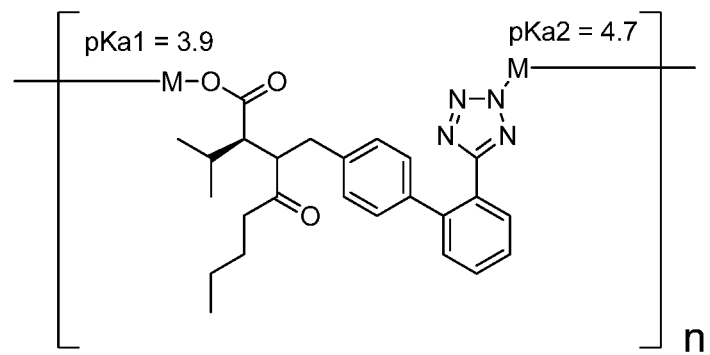
FIG. 13 is a theoretical structure showing a coordination motif between the dianion of valsartan and a divalent metal cation leading to the repeating unit of a coordination polymer. The $pK_a$ of the carboxylic acid is 3.9; the $pK_a$ of the tetrazole is 9.6.

The data in FIG. 7 demonstrate a clear advantage for metal coordinated liothyronine with respect to simulated Cytomel. [Zn(d-T3)]$_n$ displayed a delayed time to maximum concentration ($t_{max}$=6 hours vs 4 hours). [Zn(T3)]$_n$ exhibited a blunted Cmax with crossover occurring at 10 hours. These data illustrate useful modifications of pharmacokinetic properties for zinc coordinated liothyronine compounds.

Example 11

In a series of experiments similar to those described in Example 10, plasma concentration vs time curves (plasma profiles) were generated for Na(HT3), Zn(HT3)2, and [Zn(T3)]$_n$ in male Sprague Dawley rats after oral administration. Pharmacokinetic parameters relevant to evaluating controlled release performance, Cmax, FWHM, and AUC, were measured and appear in Table 4.

Duodenum targeting (D) is accomplished by hand coating caps with Eudragit L100-55 (Acryl-Eze, water solvent) designed to dissolve in the duodenum at pH ca. 5.5. Stomach targeting (S) is by using uncoated gel caps.

The Full Width at Half Maximum (FWHM), where Width is measured along the time axis, and Half Maximum is ½Cmax, is a parameter used to evaluate the degree of extended release of drug absorption. Both zinc coordinated liothyronine compounds tested display a longer absorption phase than simulated Cytomel. Zn(HT3)$_2$ displays a blunted Cmax with respect to simulated Cytomel with a comparable AUC.

TABLE 4

Average Cmax, FWHM, and AUC of compounds tested.

| Exp No. | Compound | Cmax (ng/mL) average | FWHM (hours) average | AUC (ng-hr/mL) average | Target |
|---|---|---|---|---|---|
| 1 | Zn(HT3)$_2$ | 0.24 | 16.6 | 3.45 | D |
| 2 | [Zn(T3)]$_n$ | 0.76 | 12.3 | 9.09 | D |
| 3 | Na(HT3) | 0.45 | 4.9 | 3.71 | S |

Although the invention herein has been described in connection with described embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

What is claimed is:

1. A supramolecular polymeric structure, comprising:
   a metal coordination complex, wherein the metal coordination complex comprises [ZnA$_p$T3(H$_2$O)$_q$] and where
   Zn is zinc;
   T3 is triiodothyronine;
   A is an adjuvant;
   p is 0-10;
   q is 0-20.

2. The structure of claim 1, which is insoluble in water.

3. The structure of claim 1, wherein the T3 demonstrates a controlled release from the complex when administered to a patient.

4. The structure of claim 1, wherein the adjuvant is selected from aromatic dicarboxylic acids, phenols, and catechols.

5. The structure of claim 4, wherein the adjuvant is tyrosine.

6. A pharmaceutical composition comprising the structure of claim 1 and a pharmaceutically acceptable carrier.

7. The composition of claim 6, wherein the composition demonstrates a controlled release of T3.

8. A method of treating a patient having a disease comprising administering a therapeutically effective amount of the supramolecular polymeric structure of claim 1 to the patient in need thereof.

9. The method of claim 8, wherein the disease is hypothyroidism.

10. A method of increasing a mucoadhesive property of T3, comprising forming a supramolecular polymeric structure according to claim 1 by mixing T3, and optionally an adjuvant, with Zn to form a precipitate; and filtering the precipitate to obtain $[ZnA_pT3(H_2O)_q]$.

11. The structure of claim 1, wherein, q is 3.
12. The composition of claim 6, wherein q is 3.
13. The method of claim 10, wherein q is 3.
14. The structure of claim 1, wherein p is 1.
15. The structure of claim 11, wherein p is 1.
16. The composition of claim 6, wherein p is 1.
17. The composition of claim 12, wherein p is 1.
18. The method of claim 10, wherein p is 1.
19. The method of claim 13, wherein p is 1.

* * * * *